United States Patent [19]

Cohen et al.

[11] Patent Number: 5,179,915
[45] Date of Patent: Jan. 19, 1993

[54] ANATOMICALLY MATCHING INTRAMEDULLARY ALIGNMENT ROD

[75] Inventors: Robert C. Cohen, Rockaway; Scott V. Cron, Rahway, both of N.J.

[73] Assignee: Osteonics Corporation, Allendale, N.J.

[21] Appl. No.: 818,635

[22] Filed: Jan. 6, 1992

[51] Int. Cl.$^5$ .............................................. A61F 5/04
[52] U.S. Cl. ..................................... 606/62; 606/64; 606/86
[58] Field of Search ....................... 606/60, 62, 64, 67, 606/81, 84–88, 96, 98

[56] References Cited

U.S. PATENT DOCUMENTS

| | | |
|---|---|---|
| 2,985,168 | 5/1961 | Jonas et al. |
| 3,118,444 | 1/1964 | Serrato, Jr. |
| 3,433,220 | 3/1969 | Zickel |
| 3,977,398 | 8/1976 | Burstein |
| 4,103,683 | 8/1978 | Neufeld |
| 4,261,351 | 4/1981 | Scherfel |
| 4,281,649 | 8/1981 | Derweduwen |
| 4,446,857 | 5/1984 | Otte et al. ............... 606/62 |
| 4,474,177 | 10/1984 | Whiteside |
| 4,487,203 | 12/1984 | Androphy |
| 4,522,202 | 6/1985 | Otte et al. ............... 606/62 |
| 4,913,137 | 4/1990 | Azer et al. ............... 606/64 |
| 4,952,213 | 8/1990 | Bowman et al. ......... 606/62 X |
| 5,002,545 | 3/1991 | Whiteside et al. ....... 606/88 X |
| 5,034,012 | 7/1991 | Frigg ...................... 606/64 X |
| 5,035,697 | 7/1991 | Frigg ...................... 606/72 X |
| 5,041,115 | 8/1991 | Frigg et al. .............. 606/62 |
| 5,066,296 | 11/1991 | Chapman et al. ........ 606/62 X |

FOREIGN PATENT DOCUMENTS 332857 9/1989 European Pat. Off. .............. 606/72
2440045 10/1975 Fed. Rep. of Germany .

OTHER PUBLICATIONS

Campbell's Operative Orthopaedics, vols. One and Two, Sixth Edition 1980, Editors Allen S. Edmonson, M.D. and A. H. Crenshaw, M.D.
The Sampson Femoral Fluted IM Implant Systems Technical Brochure The Sampson Corporation 1976.
R.M.C. Total Knee System, Richards Manufacturing Co., Inc. 1978.
Alignment of Total Knee Components, Richard S. Laskin, M.D. Jan. 1984, vol. 7, No. 1.
Knee Replacement Using the Insall/Burstein Total Condylar Knee System Zimmer USA, Inc. 1980.
Surgical Protocol, Multiflex Total Knee System, The 3M Company.
Whiteside Ortholoc, Dow Corning Wright 1983.

Primary Examiner—Robert A. Hafer
Assistant Examiner—Sam Rimell
Attorney, Agent, or Firm—Lerner, David, Littenberg, Krumholz & Mentlik

[57] ABSTRACT

An intramedullary alignment rod for properly orienting and supporting a cutting guide or tool has a complex geometry which includes at least two differently sized sections, the smaller of which is at the proximal end of the rod. The complex geometry of the rod maximizes the rigidity of the rod while avoiding the trauma of an interference fit, and facilitates stabilization of the intramedullary rod in the medullary canal.

14 Claims, 2 Drawing Sheets

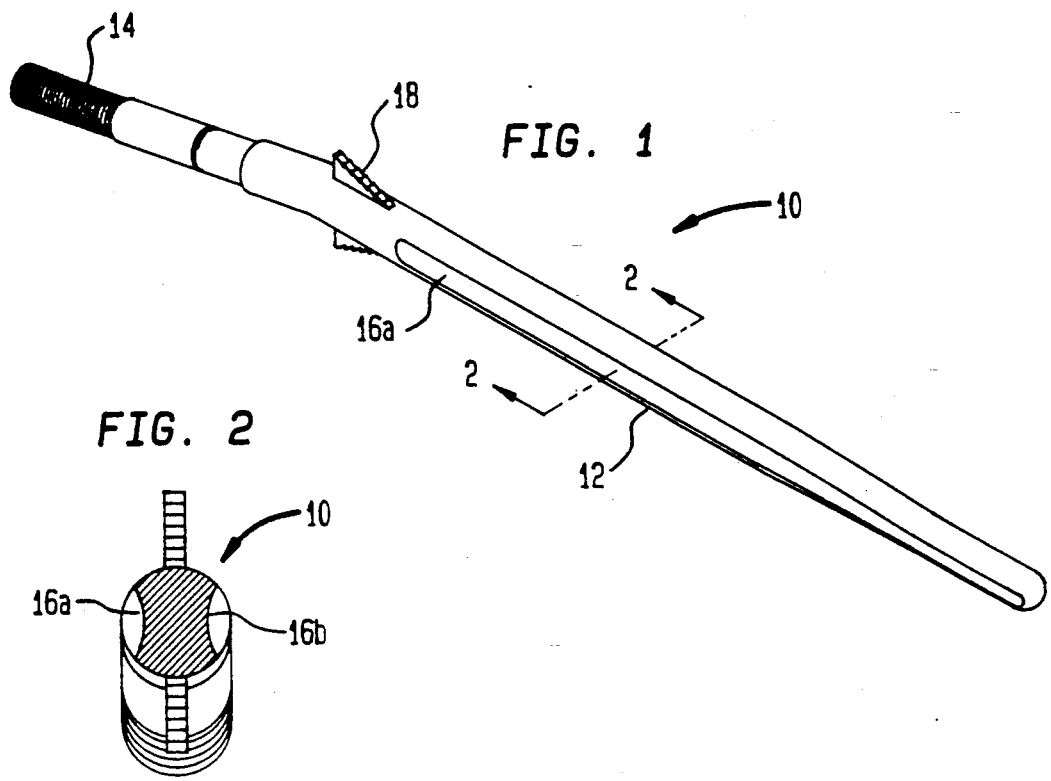
FIG. 1
FIG. 2
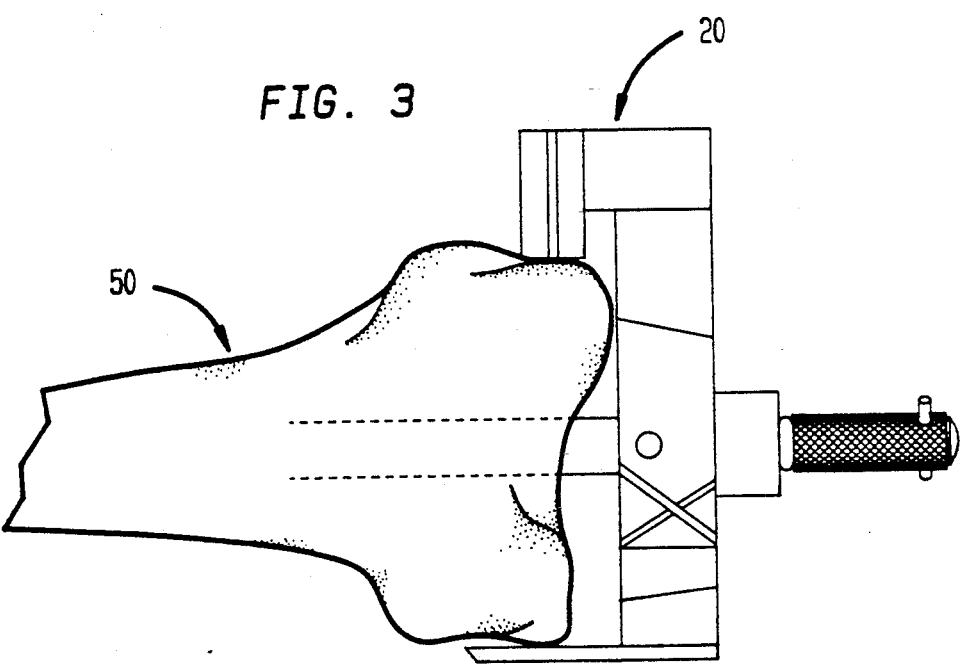
FIG. 3

ANATOMICALLY MATCHING INTRAMEDULLARY ALIGNMENT ROD

BACKGROUND OF THE INVENTION

The present invention relates generally to the preparation of the end of a bone to receive an implant, and more particularly to an instrument to facilitate the resection or shaping of the end of a bone.

In preparing a bone to receive an implant, it has been recognized that resection or shaping tools must be properly oriented with respect to the bone so that the implant to be secured to the resected or shaped surface of the bone fits properly and can provide the requisite support, freedom of movement, durability, stability, etc. While this is true of implants for virtually every joint of the human body, particular attention has been dedicated to the knee joint since the knee joint must be capable of supporting the weight of the human body and withstanding substantial shock and pounding, as well as having freedom of movement.

In preparing a knee joint to receive a total knee implant, the distal end of the femoral bone and the proximal end of the tibial bone must be prepared to receive the components of the knee implant. Since proper orientation and fit of the knee implant will provide for the best performance for the knee implant, the end of the femoral and tibial bones must, in most cases, be resected, shaped, or otherwise prepared with reference to the skeletal arrangement of the bones, the size and shape of the bones and the condylar surfaces, etc. Thus, the cutting or shaping guides used to facilitate the shaping of the end of the femoral and tibial bones must be properly oriented and secured to provide accurate and reproducible cuts. Such cutting or shaping guides are often secured on rods or other means which provide proper alignment and/or orientation.

With regard to the preparation of the distal end of the femoral bone, it is necessary to properly orient the cutting block or other guide with respect to the mechanical axis of the femoral bone, the mechanical axis being defined by a line drawn between the center of the femoral head, which sits in the hip socket, and the center of the intercondylar notch (between the condyles at the distal end of the femoral bone). In order to prepare the distal end of the femoral bone so that the knee prosthesis provides the requisite support, freedom of movement, durability, stability, etc., the cutting block must be oriented so that the distal cut at the distal end of the femoral bone is 90° to the mechanical axis of the femoral bone. Thus, it has been recognized that the mechanical axis of the femoral bone must be identified or otherwise taken into account prior to preparing the distal end of the femoral bone.

One method of properly orienting a cutting block or guide at the distal end of the femoral bone is to utilize preoperative and/or intraoperative radiographs to facilitate the identification of the mechanical axis. Another method, which might be used in conjunction with radiographs, is to use an external alignment rod which is placed in line with the femoral head and the center of the intercondylar notch. One of the shortcomings of this method is that the femoral head is difficult to locate externally.

It has also been recognized that the anatomical axis of the femoral bone, defined by a line beginning in the intercondylar notch and extending along the center of the femoral shaft, has a relationship to the mechanical axis of the femoral bone. In particular, because of the cantilever arrangement of the femoral head, the anatomical axis of the femoral bone is offset from the mechanical axis of the femoral bone by a certain degree, typically having a magnitude of 5° to 8°, though it is recognized that the angle of the offset may be outside of this range for particularly short or particularly tall individuals or due to a deformity in the femoral bone.

In view of the relationship between the anatomical axis and the mechanical axis of the femoral bone, it naturally followed that rather than identifying the mechanical axis of the femoral bone, the mechanical axis can simply be taken into account by utilizing the anatomical axis of the femoral bone, which can be approximated more easily than the mechanical axis. One method of properly orienting a cutting block or guide to make the distal cut on the femoral bone is to utilize a long external alignment rod whereby the surgeon places the external alignment rod parallel to the femoral shaft in both the anterior-posterior and medial-lateral planes. The surgeon would then know approximately where the mechanical axis of the femoral bone would lie so that the cutting block or guide could be arranged, with the appropriate angular adjustment, to make the distal cut with respect to the approximated mechanical axis. Of course, since the bone itself could not be seen during external orientation of the alignment rod with the femoral shaft, and particularly when operating on obese patients, there may be some error in properly orienting the cutting block or guide, or the holding means therefor. The use of an intraoperative radiograph may improve such external orientation, but the surgical procedure then becomes more time-consuming, tedious, and is still subject to error.

Accordingly, it was recognized that the use of an intramedullary alignment rod inserted into the medullary canal of the bone could be used to take into account the mechanical axis of the femoral bone without having to identify such mechanical axis beyond a preoperative radiograph to determine or approximate the angle between the mechanical axis and the anatomical axis. Such an intramedullary alignment rod is a properly oriented means for holding the cutting guide. Of course, some surgeons may still choose to use any one or both of the above-described methods of taking intraoperative radiographs and using an external alignment rod to check alignment of the cutting guide and/or the intramedullary rod.

The use of intramedullary alignment rods has been widespread. Examples of such intramedullary alignment rods are that which is disclosed in U.S. Pat. No. 4,487,203 to Androphy, the IM rod of the Multiflex Total Knee System by the Surgical Products Division of 3M Company, the IM rod of the R.M.C. Total Knee System by Richards Manufacturing Co., Inc. and that which is disclosed in the paper entitled, "Knee Replacement Using the Insall/Burstein Total Condylar Knee System" by John Insall, M.D. and Albert H. Burstein, Ph.D. for the New York Society for the Relief of the Ruptured and Crippled. As the above-cited examples reveal, several different expedients have been used in connection with intramedullary alignment rods to orient the cutting guide with respect to the mechanical axis of the femoral bone. For instance, in the Androphy patent, the intramedullary rod includes a long portion which extends into the medullary canal of the femoral bone and a short external portion which extends from the long portion at a 90° angle and on which a cutting block can be provided. The cutting block on the short external portion can then be rotated so that the cutting block is oriented to guide the distal cut at 90° to the mechanical axis of the femoral bone. In the 3M Multiflex Total Knee System, the rod is bent at a preselected angle so that the bent portion which extends externally of the femoral bone is approximately in line with the mechanical axis of the femoral bone. A cutting and/or drilling guide can then be placed on the bent portion so that a distal cut guide surface on the cutting block is 90° to the bent portion, and consequently to the mechanical axis. The rod of the R.M.C. Total Knee System is similar to that of the 3M Multiflex System. In the article regarding the Insall/Burstein Total Condylar Knee System, a long IM rod is shown and discussed for use in the tibia where the rod extends from the proximal end almost to the ankle. In addition to the above systems, the use of a straight alignment rod has also been proposed whereby the hole in the cutting block which is to be supported on the straight alignment rod is bored at a preselected angle to the distal cut guide surface, and all other guide surfaces on the cutting block are referenced from the distal cut guide surface.

Because of the anatomical shape of the medullary canal of the femoral bone, tapering from wide to narrow and having a degree of curvature, those in the art have considered the use of longer intramedullary alignment rods to more accurately approximate the anatomical axis of the femoral bone. In a paper entitled, "Alignment of Total Knee Components", by Richard S. Laskin, M.D., published in the January 1984 issue of Orthopedics, Dr. Laskin describes his experience with various alignment systems. In this paper, Dr. Laskin not only concluded that the degree of accuracy in utilizing an intramedullary alignment rod far surpassed the degree of accuracy obtained by using either the method of identifying the mechanical axis by locating the femoral head or the use of the external alignment rod where the external aspect of the femoral shaft is used for reference, but also concluded that a longer intramedullary alignment rod provided more accurate results than a shorter intramedullary alignment rod.

Since the femoral canal tapers from a relatively wide portion at the distal end to the isthmus, typically considered to be the narrowest portion of the medullary canal in cross-section, though it may vary, and since the anatomical axis of a femoral bone is believed to pass along the center of the femoral shaft, it has been postulated that the isthmus provides the most accurate approximation of the anatomical axis of the femoral bone; even though the isthmus itself is curved in many cases, and it is difficult to precisely define the same. However, even at the time of the 3M Multiflex System and the Richards R.M.C. System, it was thought that an intramedullary alignment rod which approaches the isthmus, which in most cases will have a length and is not a single point in the canal, and does not necessarily extend through the isthmus would suffice to provide proper orientation of the intramedullary alignment rod for supporting a cutting guide in appropriate relation to the mechanical axis, as taken into account by the approximation of the anatomical axis of the femoral bone. If there were any error in the approximation of the anatomical axis by reason of the rod not extending into and/or through the isthmus, such error would be considered insignificant in properly orienting the cutting block with respect to the mechanical axis; especially since even rods which do extend into and/or through the isthmus might result in error for a variety of reasons, including the rod did not extend through the center of the canal or the canal itself simply did not provide the best approximately of the anatomical axis.

Others have taken the approach that to provide the most accurate approximation of the anatomical axis of the femoral bone, it is necessary not only to extend into and through the isthmus, but also to provide a close fit within the isthmus. Thus, in U.S. Pat. No. 4,474,177 to Whiteside, a method is taught whereby the surgeon is to first ream the medullary canal with a reamer having a diameter which approximates the diameter of the isthmus, followed by the use of an intramedullary alignment rod which has an extramedullary portion which is set at a preselected angle to the intramedullary portion. The intramedullary portion must be long enough to extend into and through the isthmus, and must have a large enough diameter (larger than the reamer) such that it is bound by the cortical bone which forms the isthmus. Accordingly, an "interference fit" results to purportedly provide the proper orientation as well as stability of the alignment rod.

The interference fit taught in the Whiteside patent is undesirable since it requires a reaming step in which a reamer is inserted past the isthmus of the femoral bone such that the axis of the reamer hopefully coincides with the anatomical axis of the femoral bone. The use of the reamer is intended to follow the normally curved medullary canal of the femoral bone and cut any portions of the cortical bone which might be in the way. Such reaming is not only time consuming and requires additional effort on the part of the surgeon, but more importantly, it causes a disturbance in the medullary canal and the cortical bone surrounding the medullary canal. In fact, such an interference fit of the rod might cause a fat embolism which even fluting on the rod could not prevent. Still further, the reamer used in the procedure taught by Whiteside could very well cut into the cortical bone surrounding the canal, thereby possibly redefining the shape of the canal and possibly the isthmus of the canal. The alignment rod in Whiteside is fit into the medullary canal after the reamer is removed, the alignment rod being bound by cortical bone. One must also be careful in utilizing the rod which is larger than that which has been reamed since too tight a fit in the canal could cause the bone to shatter upon insertion of the rod.

The present invention obviates the above shortcomings while providing a rigid alignment rod which facilitates proper orientation and stability of a tool guide or tool for preparing the end of a bone.

SUMMARY OF THE INVENTION

The present invention relates to an intramedullary alignment rod for properly orienting and supporting a tool guide or a tool so that the end of a bone can be prepared with accurate and reproducible cuts and/or shaping. The rod includes an internal portion for insertion into the medullary canal of a bone so that such internal portion at least approaches the isthmus of the bone, means at the distal end of the rod for receiving a tool guide or a tool itself, the internal portion having at least a small section and a large section and whereby the small section is at the proximal end of the rod and is sufficiently small so as to avoid an interference fit of the same in the medullary canal, and whereby the large section is sufficiently large so as to provide the rod with rigidity.

In the preferred embodiment, the rod is tapered from the large section to the small section, though the transition zone from the large section to the small section may be characterized by a single or multiple stepped configuration. In addition, the transition zone is preferably close to the distal end of the rod, while avoiding an interference fit of the larger section of the rod in the medullary canal. Still further, the continuous taper of the internal portion from the large section to the small section preferably approximates the taper of the medullary canal approaching the isthmus of the bone. The length of the internal portion is preferably approximately 8 inches.

The rod can also be circular in cross section, and include flutes on either side to permit air or fluids to escape as the rod is being inserted into the medullary canal. The rod can be a femoral alignment rod where the taper would approximate the tapered medullary shape of the femoral medullary canal approaching the isthmus of the femoral bone. In addition, the rod can include means for taking into account the mechanical axis of the femoral bone. Still further, the rod can include at least two stabilizing fins at the distal end for stabilizing the intramedullary alignment rod in the medullary canal.

Accordingly, it is an object of the present invention to provide an intramedullary alignment rod of complex geometry which maximizes the rigidity of the rod while avoiding the trauma of an interference fit in the medullary canal of a bone.

It is another object of the present invention to provide an intramedullary alignment rod to properly orient and support a cutting block or guide for resecting or shaping the end of a bone without creating a disturbance to the bone.

It is another object of the present invention to provide an intramedullary alignment rod having at least two sizes or diameters, the smaller of which is at the proximal end of rod and is so sized that it will not disturb the medullary canal in the area of the isthmus.

The foregoing and other objects can be accomplished by providing an intramedullary alignment rod having an elongate internal portion for insertion into the medullary canal of a bone, the internal portion having a first end and a second end and being of such a length that it at least approaches the isthmus of the bone, the internal portion also having at least two sections, each being of a different cross-sectional size, the smallest of the at least two sections being at the first end and being sufficiently small with respect to the medullary canal so as to avoid an interference fit of the same in the medullary canal, the larger of the at least two sections being sufficiently large so as to provide a rigid support for a tool guide or tool, and means for receiving a tool guide or tool, such means being at the second end of the internal portion.

BRIEF DESCRIPTION OF THE DRAWINGS

The foregoing and other objects of the present invention will become apparent, as will a better understanding of the concepts underlying the present invention, by reference to the description which follows and to the accompanying drawings in which:

FIG. 1 is a plan view (anterior-posterior) of an intramedullary alignment rod in accordance with the present invention;

FIG. 2 is a cross-section taken on line 2—2 in FIG. 1;

FIG. 3 is an elevational view (medial-lateral) of the distal end of a femoral bone with an intramedullary alignment rod supporting a femoral cutting block;

DETAILED DESCRIPTION OF THE INVENTION

Figure 4A:
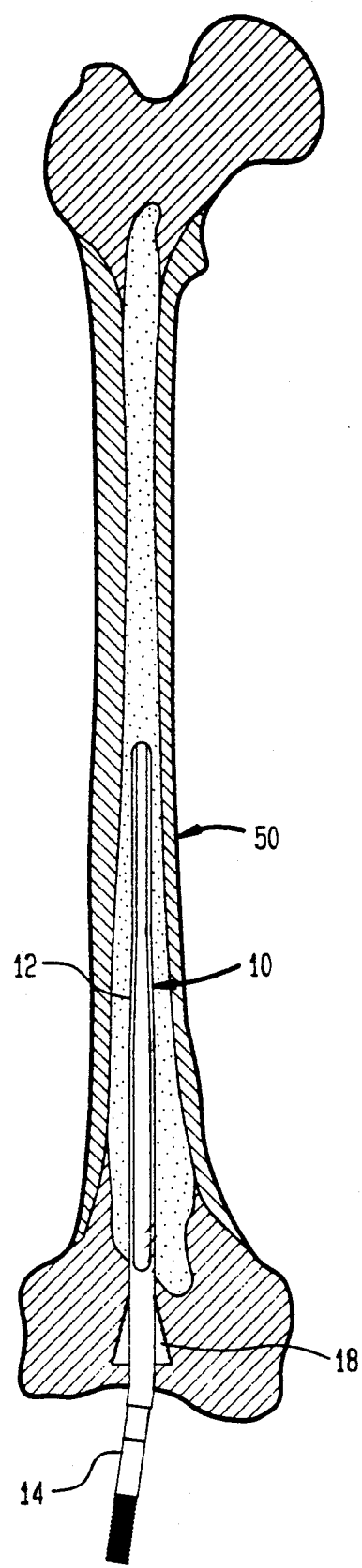
FIG. 4A is a cross-sectional view of a right femoral bone showing the intramedullary alignment rod of FIG. 1 in place in the medullary canal.

Referring to the figures, an intramedullary alignment rod generally designated as 10 is illustrated. The intramedullary alignment rod 10 is intended for use in connection with a cutting guide generally designated as 20 in FIG. 3 which shows the cutting guide 20 in a fixed position at the distal end of a femoral bone 50, as supported by the rod 10. The particular cutting guide 20 shown in FIG. 3 is constructed so that it can provide guidance for the distal cut, the anterior cut, the anterior chamfer cut, the posterior chamfer cut and the posterior cut. The slots through the cutting guide 20 are used to facilitate such cuts.

The rod 10 includes an internal portion 12, which is intended to be inserted into the medullary canal of a femoral bone, and an external portion 14, which is intended to support the cutting guide 20 at the distal end of the femoral bone 50. As can be seen in at least FIG. 1, external portion 14 is at an angle to internal portion 12. As indicated above, the purpose of having the external portion 14 at an angle to the internal portion 12 is to provide an approximation of the mechanical axis of the femoral bone. Of course, as is well known in the art, the extent to which the external portion 14 is offset from the internal portion 12 will depend upon several factors, not the least of which is whether a varus or valgus alignment correction required with respect to the femoral bone and/or tibial bone. Thus, as the rod 10 is shown in FIG. 1 (that is, in the anterior-posterior view), the rod 10 is arranged for use in a left femoral bone. However, since it is desirable to provide only one intramedullary alignment rod for knee replacements in either the left or right legs, the rod 10 as shown in FIG. 1 can be rotated 180° whereby it would be arranged for use with a right femoral bone, as are the rods shown in FIGS. 4A and 4B.

The rod 10 is fluted on two sides, as can be seen in FIGS. 1 and 2. The flutes 16a and 16b are tapered from large to smaller from the distal end of the rod 10 to the proximal end of rod 10. As is known in the art, the flutes are provided to permit air or fluids to escape as the alignment rod enters and occupies space in the medullary canal.

The rod 10 as shown herein and in the preferred embodiment is approximately 8.3 inches in length so that when the rod 10 is in place in the femoral bone 50, the tip of the internal portion 12 approaches the isthmus of the femoral bone 50, and may even be said to be partially in the isthmus. The length can, of course, be varied.

Significantly, the rod 10 includes a tapered geometry, whereby the first approximately 4.3 inches is approximately 0.33 inches in diameter, and the next approximately 1.5 inches is characterized by a continuous taper from approximately 0.33 inches at the distal end to approximately 0.25 inches at the proximal end. Thus, from approximately 5.8 inches to approximately 8.3 inches, the rod is at 0.25 inches in diameter. Of course, different diameters may be provided at the proximal and distal ends of the rod 10, the cross-section may be other than substantially circular, and the transition from the distal diameter to the proximal diameter need not be a continuous taper. Rather, a single or multiple stepped configuration is also contemplated. What is significant is that the geometry of the rod provides rigidity through a varying area moment of inertia.

Thus, in accordance with the present invention, the relatively small diameter at the proximal end of the rod 10 will avoid an interference fit of the rod 10 in the isthmus of the femoral bone 50, while the complex geometry of the rod 10 provides the rod 10 with rigidity which might not otherwise be present in an alignment rod which is 0.25 inches throughout its length. Such larger diameter also provides a more solid workpiece at the distal end of the rod 10 for receiving and supporting the cutting guide 20 or any other guide member or tool.

Of course, different lengths, diameters and geometry are contemplated since embodiments other than the preferred embodiment shown and described herein will provide the advantages of the present invention, and also since femoral bones differ from person to person. Indeed, to the extent that a particular alignment rod may be too long or short or have too large a diameter (at any of the sections) for a particular bone, whether it be by reason of a deformity or simply by reason of the femoral bone being particularly long or short, a differently sized rod can be utilized.

Figure 4B:
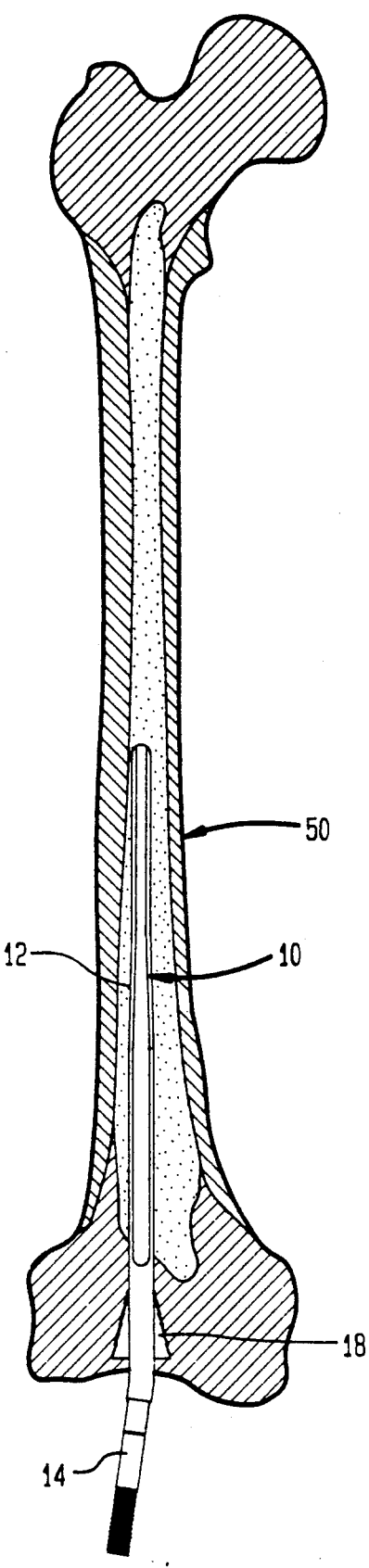
FIG. 4B is a cross-sectional view (anterior-posterior) of a right femoral bone showing the intramedullary alignment rod of FIG. 1 in a slightly different place in the medullary canal than that which is shown in FIG. 4A.

In FIG. 4A, the rod 10 is shown in place in the medullary canal of the femoral bone 50. The rod 10 is inserted into the femoral medullary canal following the drilling of an entrance hole in the intercondylar notch. When in the position shown in FIG. 4A, rod 10 can receive the cutting guide 20 or any other guide or tool which can properly orient the same with respect to the mechanical axis of the femoral bone 50. As can be seen in FIG. 4A, during insertion, the rod 10 traveled almost through the center of the medullary canal as viewed from anterior to posterior. Thus, there is almost an equal amount of space on either side of the rod 10 in the medullary canal. This is an example of how the rod might be disposed in the medullary canal after insertion. Another example of how the rod 10 might be disposed in the medullary canal is shown in FIG. 4B. In FIG. 4B, the rod 10 traveled more laterally through the canal such that there is little or no space on the lateral side of the canal and there is a large amount of space on the medial side of the canal.

It is recognized that the rod 10 will not follow the same path in each and every femoral bone. However, the complex geometry of the rod 10 in accordance with the present invention, tapered in the preferred embodiment, enables the proximal end of the rod 10 to approach or enter the isthmus without being bound by the cortical bone, while retaining the rigidity required of an alignment rod so that, for example, the rod does not chatter or vibrate when a cutting tool is in use and will resist bending during insertion. Also, while the middle or distal end of the rod 10 may even contact one side of the medullary canal, this does not prevent the proximal end of the rod 10 from approaching or entering the isthmus in order to provide proper orientation. In fact, in some cases, the contact of the larger diameter section of the rod 10 nearer to the distal end of the canal could serve to facilitate stabilization of the rod 10, though it is recognized that most of the stabilization of the properly oriented rod 10 is achieved through the use of stabilizing fins, discussed below.

Thus, providing the larger and smaller sections enables the larger section to contact the bone in a wider area of the canal (distally if in the femur) while still permitting the smaller section to approach or even enter the isthmus without machining the medullary canal and/or without the trauma of an interference fit. If and when this occurs, the smaller section or even another section of the internal portion of the rod may also contact the bone at another area or areas of the canal. Therefore, stabilization of the rod might also be facilitated by a multiple (at least two) point contact of the cortical bone in the intramedullary canal, whereas the contact is at different areas of the canal.

Once the rod 10 is in position within the medullary canal as shown in either of FIGS. 4A or 4B (or any other position the rod might attain in the canal), the cutting guide 20 can be secured to the external portion 14. The requisite cuts can then be made to the distal end of the femoral bone 50 to prepare the same to receive a knee implant or at least the femoral component of a knee implant.

The rod 10 also includes two stabilizing fins 18 which are arranged on the rod 10 on diametrically opposite sides at the distal end of the rod 10. It is specifically noted that the fins 18 are arranged in the same plane as the external portion 14. As shown in FIG. 1, the fins 18 extend from the rod 10 at a relatively small angle so s to prevent the possibility of cracks in the cortical bone surrounding the entrance hole made at the distal end of the femoral bone. In addition, each fin 18 includes a series of teeth, each of which teeth include an inclined surface or ramp (front rake) on which the cortical bone surrounding the hole made at the distal end of the femoral bone can ride as the rod 10 is being inserted into the medullary canal, and a back rake on which the cortical bone can rest as it rides over and passes over the inclined surface. Thus, a ratchet and pawl action is provided for by the structure of such teeth.

While the foregoing description and figures illustrate the preferred embodiment of the intramedullary alignment rod in accordance with the present invention, it should be appreciated that certain modifications can be made and are encouraged to be made in the structure of the disclosed embodiments without departing from the spirit and scope of the present invention which is intended to be captured by the claims set forth immediately below.

What is claimed is:

1. A tool guide support rod for supporting a tool guide or a tool, said rod comprising:
an elongate internal portion for insertion into the medullary canal of a bone, said internal portion being at least about eight (8) inches in length and having a distal end and a proximal end;
said internal portion having at least two sections, each being of a different cross-sectional size, the smallest of said at least two sections being at said distal end and being approximately 0.25 inches in cross-sectional size and being provided along a minor portion of the length of said internal portion such that the smallest section normally avoids an interference fit with the medullary canal, and the larger of said at least two sections being sufficiently large so as to provide a rigid support for the tool guide or tools; and means for receiving a cutting tool guide or cutting tool, said means being at said proximal end of said internal portion.

2. The rod in claim 1, including a transition zone from the largest of said at least two sections to the smallest of said at least two sections.

3. The rod in claim 2, wherein said transition zone is as close to said first end as possible while normally avoiding an interference fit of the larger of said at least two sections in the medullary canal.

4. The rod in claim 2, wherein said transition zone is a continuous taper from the largest of said at least two sections to the smallest of said at least two sections.

5. The rod in claim 3, wherein said transition zone is a continuous taper from the largest of said at least two sections to the smallest of said at least two sections.

6. The rod in claim 4, wherein at least said transition zone and said smallest of said at least two sections are substantially circular in cross-section.

7. The rod in claim 4, wherein said continuous taper of said internal portion approximates the taper of the medullary canal approaching the isthmus of the bone.

8. The rod in claim 6, wherein said internal portion is adapted for insertion into the distal end of a femoral bone for supporting a distal femoral surface cutting guide or tool, and wherein said continuous taper of said internal portion approximates the taper of the femoral medullary canal approaching the isthmus of the femoral bone.

9. The rod in claim 8, wherein said internal portion is at least partially fluted on its outside surface.

10. The rod in claim 9, wherein the means for receiving a tool guide or tool is an elongate external portion extending from said second end of said internal portion, said external portion having an axis which is offset at an angle from the axis of said internal portion.

11. The rod in claim 8, wherein said internal portion includes longitudinal flutes on diametrically opposite sides of said internal portion, and wherein said longitudinal flutes are tapered in width from said second end to said first end of said internal portion.

12. The rod in claim 4, further comprising at least two stabilizing fins adjacent said second end of said internal portion for stabilizing said intramedullary alignment rod in the medullary canal, said stabilizing fins being adapted to be forced into the bone surrounding an entrance hole in the end of a bone.

13. The rod in claim 4, wherein said internal portion is approximately 8 inches in length.

14. The rod in claim 13, wherein said internal portion is substantially circular in cross-section, and wherein said smallest of said at least two sections is approximately 0.25 inches in diameter and the largest of said at least two sections is approximately 0.33 inches in diameter.

* * * * *